United States Patent
Kudo et al.

(10) Patent No.: US 11,181,487 B2
(45) Date of Patent: Nov. 23, 2021

(54) PHASE IMAGING METHOD AND PHASE IMAGING APPARATUS USING PHASE IMAGING METHOD

(71) Applicant: University of Tsukuba, Ibaraki (JP)

(72) Inventors: Hiroyuki Kudo, Tsukuba (JP); Songzhe Lian, Tsuchiura (JP)

(73) Assignee: University of Tsukuba, Ibaraki (JP)

( * ) Notice: Subject to any disclaimer, the term of this patent is extended or adjusted under 35 U.S.C. 154(b) by 0 days.

(21) Appl. No.: 17/250,099

(22) PCT Filed: Jun. 12, 2019

(86) PCT No.: PCT/JP2019/023266
§ 371 (c)(1),
(2) Date: Nov. 24, 2020

(87) PCT Pub. No.: WO2019/240165
PCT Pub. Date: Dec. 19, 2019

(65) Prior Publication Data
US 2021/0215624 A1    Jul. 15, 2021

(30) Foreign Application Priority Data
Jun. 12, 2018  (JP) .............................. JP2018-111563

(51) Int. Cl.
*G01N 23/041* (2018.01)
*G01N 23/083* (2018.01)
*A61B 6/00* (2006.01)

(52) U.S. Cl.
CPC ......... *G01N 23/041* (2018.02); *G01N 23/083* (2013.01); *A61B 6/484* (2013.01)

(58) Field of Classification Search
CPC .. G01N 23/041; G01N 23/083; G01N 23/046; G01N 23/20075; A61B 6/484;
(Continued)

(56) References Cited

U.S. PATENT DOCUMENTS

2011/0158493 A1  6/2011  Nagai et al.
2014/0169524 A1  6/2014  Sperl et al.
(Continued)

FOREIGN PATENT DOCUMENTS

EP        1623671 A1    2/2006
JP      2012016370 A    1/2012
(Continued)

OTHER PUBLICATIONS

"International Application Serial No. PCT/JP2019/023266, International Search Report dated Sep. 10, 2019", w/ English Translation, (Sep. 10, 2019), 8 pgs.
(Continued)

*Primary Examiner* — David P Porta
*Assistant Examiner* — Mamadou Faye
(74) *Attorney, Agent, or Firm* — Schwegman Lundberg & Woessner, P.A.

(57) ABSTRACT

A phase imaging method and apparatus are provided, the phase imaging method including causing a quantum beam from a radiation source to be incident on a detector through a test object and at least one phase grating and obtaining a phase image of the test object, based on intensity distribution of a beam in a pixel constituting the detector. The intensity distribution of the beam at least includes information of absorption ($a_0$), visibility (V), and phase ($\varphi$). At least three adjacent pixels are assumed to have a substantially identical value for each of the absorption ($a_0$), the visibility (V), and the phase ($\varphi$) through variable approximation of an image.

(Continued)

(a) FOURIER TRANSFORM METHOD (CONVENTIONAL METHOD)
(b) METHOD A ACCORDING TO INVENTION
(c) METHOD B ACCORDING TO INVENTION

The absorption, the visibility, and the phase are obtained, based on at least one measurement image.

15 Claims, 12 Drawing Sheets

(58) Field of Classification Search
CPC ..... A61B 6/4291; A61B 6/4092; A61B 6/505; A61B 6/5217; A61B 6/461; A61B 6/4035; G21K 1/106; G21K 1/067
See application file for complete search history.

(56) References Cited

U.S. PATENT DOCUMENTS

| | | |
|---|---|---|
| 2015/0308967 A1 | 10/2015 | Nagai |
| 2015/0362444 A1 | 12/2015 | Nagai |
| 2016/0343128 A1 | 11/2016 | Nitta et al. |

FOREIGN PATENT DOCUMENTS

| | | |
|---|---|---|
| JP | 2012507690 A | 3/2012 |
| JP | 2012143491 A | 8/2012 |
| JP | 2014117336 A | 6/2014 |
| JP | 2016000139 A | 1/2016 |
| JP | 2016214615 A | 12/2016 |
| WO | WO-2004058070 A1 | 7/2004 |
| WO | WO-2010050483 A1 | 5/2010 |
| WO | WO-2010050611 A1 | 5/2010 |
| WO | WO-2017013153 A1 | 1/2017 |

OTHER PUBLICATIONS

"International Application Serial No. PCT/JP2019/023266, Written Opinion dated Sep. 10, 2019", (Sep. 10, 2019), 6 pgs.

Arboleda, C., et al., "Tilted-grating approach for scanning-mode X-ray phase contrast imaging", Opt. Express 22 (13), (2014), 15447-15458.

Bravin, A., et al., "X-ray phase-contrast imaging: from pre-clinical applications towards clinics", Phys. Med. Biol. 58,, (2013), R1-R35.

Ge, Y., et al., "Grating based X-ray differential phase contrast imaging without mechanical phase stepping", Opt. Express 22, (2014), 14246-14252.

Kottler, C., "Grating interferometer based scanning setup for hard X-ray phase contrast imaging", Rev. Sci. Instrum. 78, (2007), 043710.

Lian, Songzhe, et al., "Phase measurement technique", Preprints of conference of the Japanese Society of Medical Imaging Technology, vol. 37, (2018), pp. 210-213.

Momose, A., et al., "Demonstration of X-Ray Talbot interferometry", Jpn. J. Appl. Phys. 42, (2003), L866-L868.

Pfeiffer, F., et al., "Neutron Phase Imaging and Tomography", Phys. Rev. Lett. 96,, (Jun. 2, 2006), 215505-1-215505-4.

Takeda, M., et al., "Fourier-transform method of fringe-pattern analysis for computer-based topography and interferometry", J. Opt. Soc. Am. 72, (1982), 156-160.

Weitkamp, T., et al., "X-ray phase imaging with a grating interferometer", Opt. Express 12 (16), (2005), 6296-6304.

FIG. 4
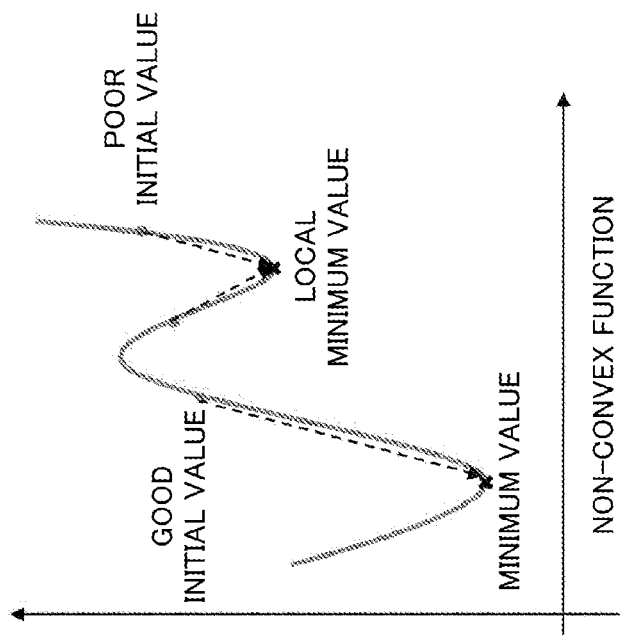
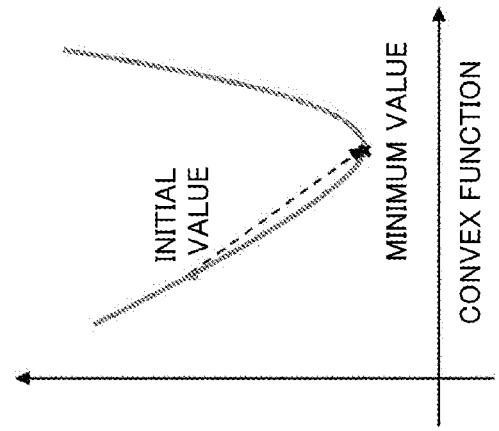

FIG. 12
(a)
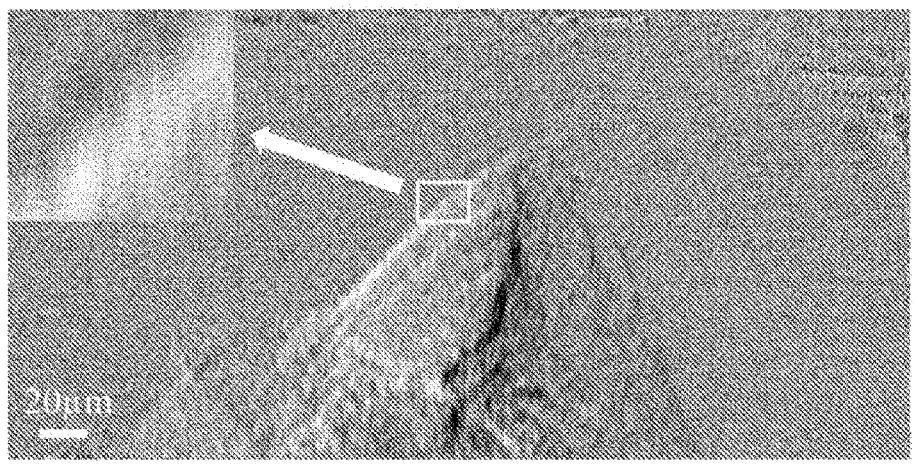
(b)
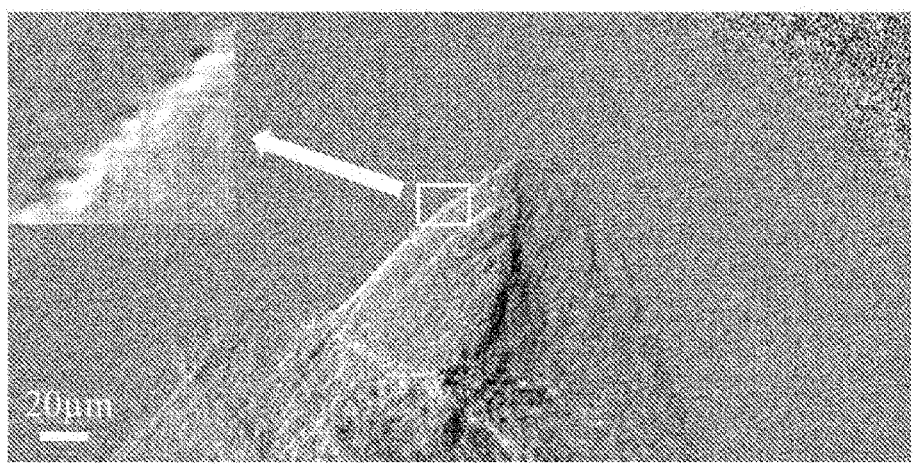
(c)
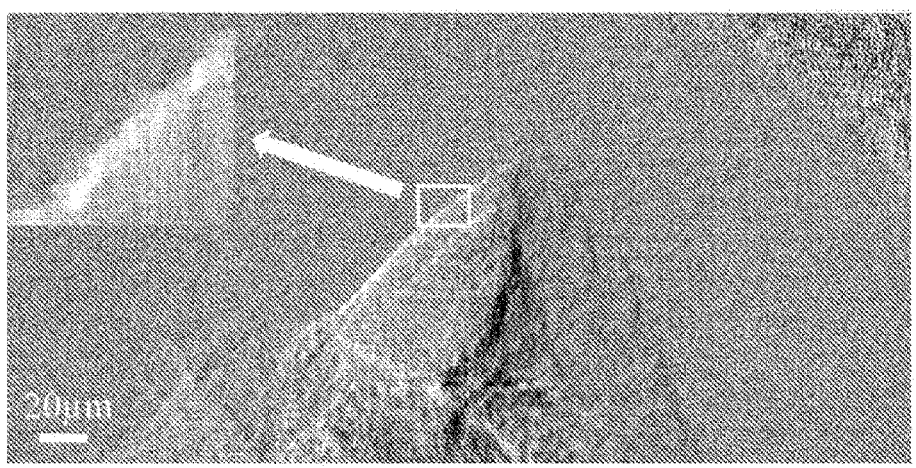

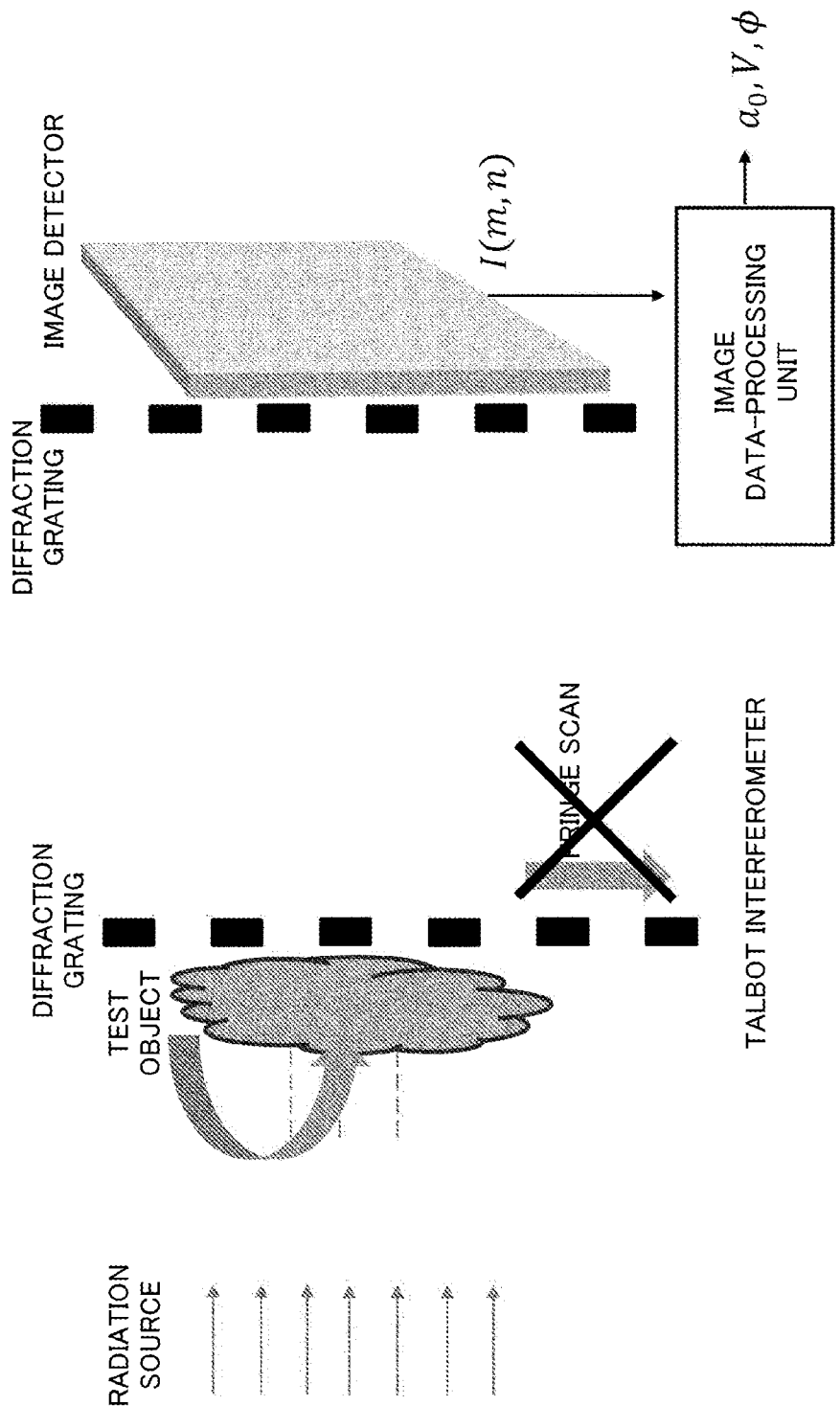

PHASE IMAGING METHOD AND PHASE IMAGING APPARATUS USING PHASE IMAGING METHOD

PRIORITY APPLICATIONS

This application is a U.S. National Stage Filing under 35 U.S.C. § 371 from International Application No. PCT/JP2019/023266, filed on Jun. 12, 2019, and published as WO2019/240165 on Dec. 19, 2019, which claims the benefit of priority to Japanese Application No. 2018-111563, filed on Jun. 12, 2018; the benefit of priority of each of which is hereby claimed herein, and which applications and publication are hereby incorporated herein by reference in their entireties.

TECHNICAL FIELD

The present invention relates to a phase imaging method of obtaining an image of a test object by using a phase change that is obtained through radiation of quantum beams such as X-rays, and further relates to a phase imaging apparatus using the phase imaging method.

BACKGROUND ART

X-rays can penetrate substances, unlike visible light. Thus, with such X-rays, an internal structure of an object can be observed. Nowadays, X-rays are applied in a wide range of fields, such as X-ray imaging at hospitals and industrial non-destructive inspection. In usual X-ray imaging, the intensity of the X-rays changes due to absorption of an object when the X-ray penetrates the object, thereby forming a contrast image. In such an apparatus using an absorption rate, the heavier the element that constitutes an object, the greater the absorption of X-rays, and an image with a higher contrast can be obtained. However, to observe an object with low absorption, for example, a light element (having a small atomic quantity) such as a soft tissue of an organism, there is a problem in that a high contrast may not easily be obtained.

In view of this, as illustrated in Citation List below, research on X-ray phase imaging methods has been conducted since the 1990s.

CITATION LIST

Patent Literature

PTL 1: WO 2004058070
PTL 2: WO 2010050483

Non-Patent Literature

NPL 1: A. Bravin, P. Coan, and P. Suortti, "X-ray phase-contrast imaging: from pre-clinical applications towards clinics," Phys. Med. Biol. 58, R1 (2013).
NPL 2: F. Pfeiffer, C. Grunzweig, O. Bunk, G. Frei, E. Lehmann, and C. David, "Neutron Phase Imaging and Tomography," Phys. Rev. Lett. 96, 215505—Published 2 Jun. 2006; Erratum Phys. Rev. Lett. 97, 0 69905 (2006).
NPL 3: A. Momose, S. Kawamoto, I. Koyama, Y. Hamaishi, K. Takai, and Y. Suzuki, "Demonstration of X-Ray Talbot interferometry," Jpn. J. Appl. Phys. 42, L866-L868 (2003).
NPL 4: T. Weitkamp, A. Diaz, C. David, F. Pfeiffer, M. Stampanoni, P. Cloetens, and E. Ziegler, "X-ray phase imaging with a grating interferometer," Opt. Express 12 (16), 6296-6304 (2005).
NPL 5: M. Takeda, H. Ina and S. Kobayashi, "Fourier-transform method of fringe-pattern analysis for computer-based topography and interferometry," J. Opt. Soc. Am. 72, 156-160 (1982).
NPL 6: Y. Ge, K. Li, J. Garrett, and G. H. Chen, "Grating based X-ray differential phase contrast imaging without mechanical phase stepping," Opt. Express 22, 14246-14252 (2014).
NPL 7: C. Kottler, F. Pfeiffer, O. Bunk, C. Grunzweig, and C. David, "Grating interferometer based scanning setup for hard X-ray phase contrast imaging," Rev. Sci. Instrum. 78, 043710 (2007).
NPL 8: C. Arboleda, Z. Wang Z, and M. Stampanoni, "Tilted-grating approach for scanning-mode X-ray phase contrast imaging," Opt. Express 22 (13), 15447-15458 (2014).

SUMMARY OF INVENTION

Technical Problem

In these methods, a phase change caused when X-rays penetrate an object is measured. In other words, by making use of the fact that a phase change when X-rays penetrate an object made of light elements is far greater than an absorption change, an image with a high contrast is generated [NPL 1]. Further, in recent years, these methods have also been applied to a radiation source of neutron beams or the like [NPL 2].

Among a large number of developed imaging methods, in particular, a phase imaging method that uses Talbot interference by using diffraction gratings has been attracting attention because a regular X-ray tube can be used to produce a compact apparatus usable in hospitals or the like.

On the other hand, in a phase imaging method, a fringe-scanning method is known as a method of recovering phase from a captured intensity distribution image [NPLs 3 and 4 and PTL 1]. In this method, diffraction gratings are moved at least three times in a grating period direction, thereby performing capturing of a plurality of images. Note that each movement distance is substantially at the sub-micron level. Thus, it is required for the apparatus to have significantly high accuracy/stability, and also to have strict management for temperature change and the like in a surrounding environment for use. In addition, three or more times of movement are required, and thus it is difficult to apply the method to dynamic measurement of a moving (or changing) object, for example, visual monitoring of cell cultivation or the like.

In view of the above, a Fourier transform method has been proposed [NPL 5 and PTL 2]. In this method, the phase is calculated by performing processing using Fourier transform on a captured interference fringe image, and the phase can be acquired with a single imaging operation. However, in the Fourier transform method, a large number of high-frequency components are lost, and thus spatial resolution is reduced. This signifies that fine structures of a test object and the like are lost.

In addition to the above, a method using a special diffraction grating [NPL 6], a method using a one-dimensional sensor [NPLs 7 and 8], and the like have been proposed. However, all of those methods require new hardware.

Under such circumstances, the present invention is made in light of the conventional technologies described above, and more specifically has an object to provide a phase imaging method that allows to acquire phase of a test object having a high spatial resolution with at least a single imaging operation without a need of improvements in an existing apparatus and equipment (in particular, without improvement/change in hardware), and a phase imaging apparatus using the phase imaging method.

Solution to Problem

In order to achieve the object described above, first, the present invention proposes a phase imaging method including causing a quantum beam from a radiation source to be incident on a detector through a test object and at least one phase grating, and obtaining a phase image of the test object, based on intensity distribution of a beam in a pixel constituting the detector, wherein the intensity distribution of the beam at least includes information of absorption ($a_0$), visibility (V), and phase ($\varphi$), at least three adjacent pixels are assumed to have a substantially identical value for each of the absorption ($a_0$), the visibility (V), and the phase ($\varphi$) through variable approximation of an image, and the absorption, the visibility, and the phase are obtained, based on at least one measurement image.

Moreover, in order to achieve the object described above, the present invention proposes a phase imaging method including causing a quantum beam from a radiation source to be incident on a detector through a test object and at least one phase grating, and obtaining a phase image of the test object, based on intensity distribution of a beam in a pixel constituting the detector, wherein weighting processing is performed that gives a weight depending on similarity between each pixel and a phase value (or structure) of the pixel to be obtained by using an approximation phase image given in advance, and subsequently, absorption, visibility, and phase are obtained based on at least one measurement image by using the weight.

In addition, the present invention proposes a phase imaging apparatus including a radiation source configured to generate a quantum beam, a holder configured to hold a test object to which a beam from the radiation source is radiated, a detector configured to receive the beam from the test object through at least one phase grating, and a processing unit configured to obtain a phase image of the test object, based on intensity distribution of the beam in a pixel constituting the detector, wherein the processing unit is the phase imaging method described above.

Advantageous Effects of Invention

According to the present invention described above, useful excellent effects can be achieved by providing a phase imaging method and a phase imaging apparatus that allow acquisition of the phase of the test object having a high spatial resolution with at least a single imaging operation without requiring improvements in an existing apparatus and equipment (in particular, without improvement/change in hardware).

BRIEF DESCRIPTION OF DRAWINGS

FIG. 4 is a diagram illustrating a convex function minimization problem related to three variables of the method A.

FIG. 12 is a diagram illustrating a phase image obtained by using the methods A and B according to the present invention by using real data obtained by imaging polymers with the Talbot interferometer, in comparison with a conventional technology.

FIG. 13 is a diagram illustrating an example of a configuration of a high-speed phase CT imaging apparatus using the Talbot interferometer to which a phase imaging method and a phase imaging apparatus according to the present invention can be applied.

DESCRIPTION OF EMBODIMENTS

In the following, embodiments of the present invention will be described. Prior to the description, here, a principle of the present invention will be described in detail with reference to the attached drawings.

Example 1

Principle of Present Invention: Method A

In an apparatus that forms interference fringes by using a radiation source that generates so-called quantum beams, including X-rays, neutron beams, visible light, and the like, what is directly measured by a detector (two-dimensional) is not phase but is intensity distribution of moiré interference fringes (or a self image due to the Talbot effect) deformed due to a test object. In general, the intensity distribution measured by the detector can be expressed as follows:

[Math. 1]

$$I(m,n)=a_0(m,n)(1+V(m,n)\cos(f(m,n)+\varphi(m,n))) \quad (1)$$

Note that $a_0$ represents absorption, V represents visibility, $\varphi$ represents differential phase (also referred to as difference phase, or simply as "phase"), and f represents a waveform representing a sine wave of the moiré interference fringes. In phase imaging, phase is obtained, and thus imaging of a background when there is no test object and imaging when there is a test object are performed. Here, f is obtained from the imaging of background. When imaging of a background cannot be performed, f can also be estimated by using a local portion of a single captured image where there is a small phase change of an object (that is, where there is small deformation of moiré interference fringes).

As described above, in Expression (1), there are three variables in each pixel of the detector, and to obtain the phase, at least three different pieces of data are required. As described above, in a conventional fringe-scanning method, a plurality of captured images are obtained through imaging by moving diffraction gratings M (M≥3) times. Then, through the use of the obtained imaged data of the plurality of images, for example, the phase is obtained with the least squares method or the like. With this method, the phase can be obtained with a high spatial resolution. However, as described above, high accuracy is required in movement of the diffraction gratings. Each movement distance of the diffraction gratings in the fringe-scanning method is uniform, and is 1/M of the period of the diffraction gratings. In general, the period of the diffraction gratings is several micrometers, and thus the movement is performed substantially at a sub-micron level. Accordingly, strict stability and the like are required for the apparatus/equipment.

The present invention provides a method that enables three variables, namely absorption ($a_0$), visibility (V), and phase ($\varphi$), to be obtained with at least a single imaging operation. As has been described in the above, to obtain the phase, at least three different pieces of data are required. In the present invention, this problem is solved by variable approximation of an image.

Figure 1:
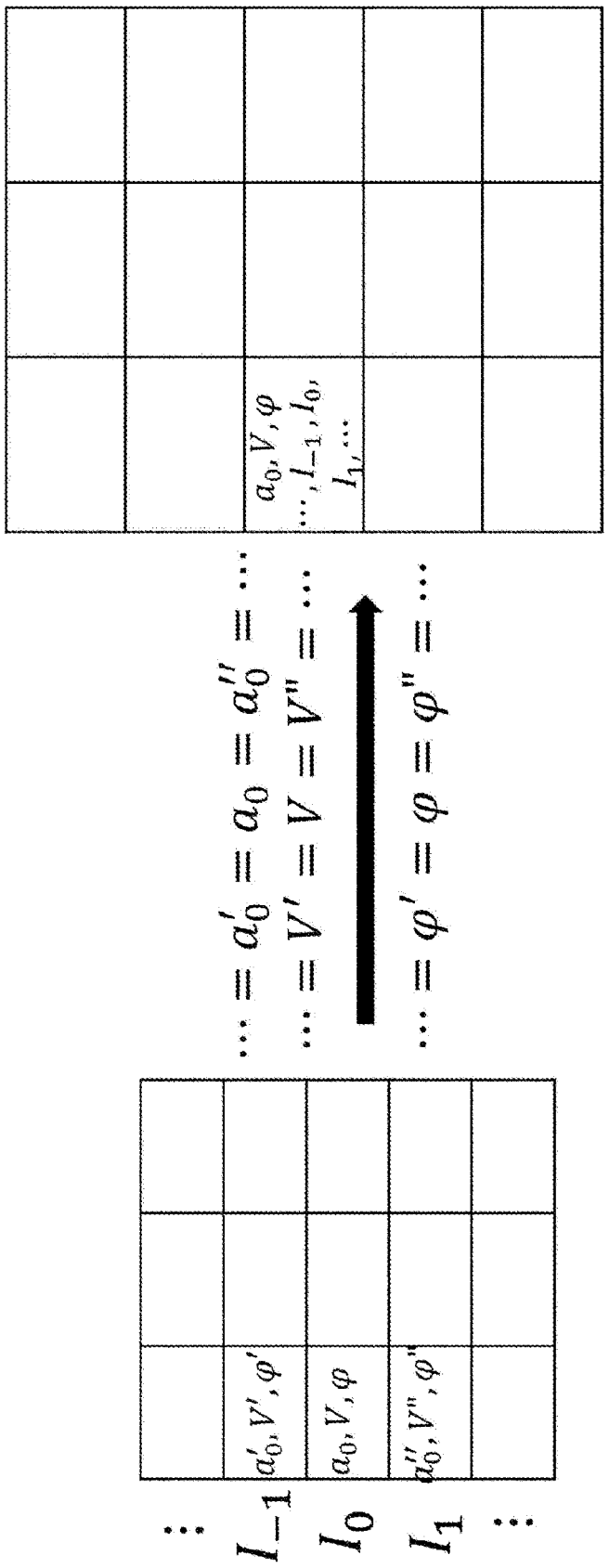
FIG. 1 is a diagram illustrating a principle of a method A according to an embodiment (Example 1) of the present invention.

Specifically, as illustrated in FIG. 1 as well, in three adjacent pixels of the detector (two-dimensional), Expression (1) shown above assumes that absorption ($a_0$), visibility (V), and phase ($\varphi$) are substantially the same as follows.

[Math. 2]

$$a_0(m,n-1)=a_0(m,n)=a_0(m,n+1), V(m,n-1)=V(m,n)=V(m,n+1) \quad (2)$$

[Math. 3]

$$\phi(m,n-1)=\phi(m,n)=\phi(m,n+1) \quad (3)$$

Note that description will be herein given using only three pixels, which similarly applies to the following description. However, as a matter of course, calculation can also be performed by using a larger number of pixels.

Under this assumption, based on Expression (1) shown above, the expression can be expressed as follows: This means that a piece of data $I_{-1}$ (m, n) is added for a pixel (m, n).

[Math. 4]

$$I(m, n-1) = a_0(m, n-1)(1 + V(m, n-1) \cos(f(m, n-1) + \phi(m, n-1))) \\ = a_0(m, n)(1 + V(m, n)\cos(f(m, n-1) + \phi(m, n))) \\ \stackrel{def}{=} I_{-1}(m, n) \quad (4)$$

In addition, according to the same approximation, as shown below, at least three pieces of data can be obtained.

[Math. 5]

$$I_{-1}(m,n)=I(m,n-1), I_0(m,n)=I(m,n), I_1(m,n)=I(m,n+1) \quad (5)$$

As described above, according to the variable approximation of the image, three pieces of data are present for three variables, and thus the phase ($\varphi$) can be obtained.

EXAMPLE

Figure 2:
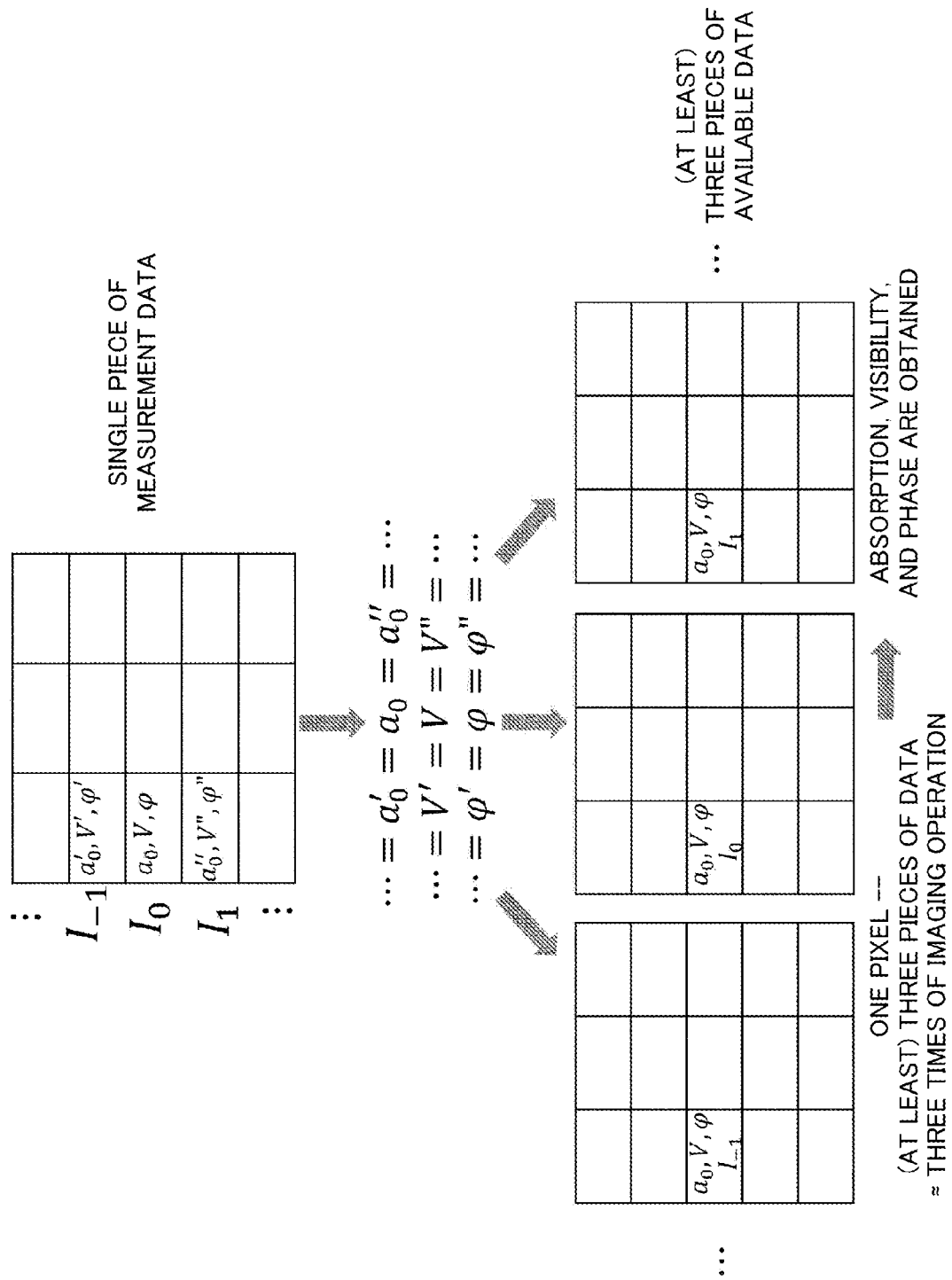
FIG. 2 is a diagram illustrating the principle of the method A.

According to the variable approximation of an image, that is, approximation by Expressions (2) and (3) shown above, as illustrated in FIG. 2 as well, the piece of data corresponding to one pixel is increased from one to three pieces.

Figure 3:
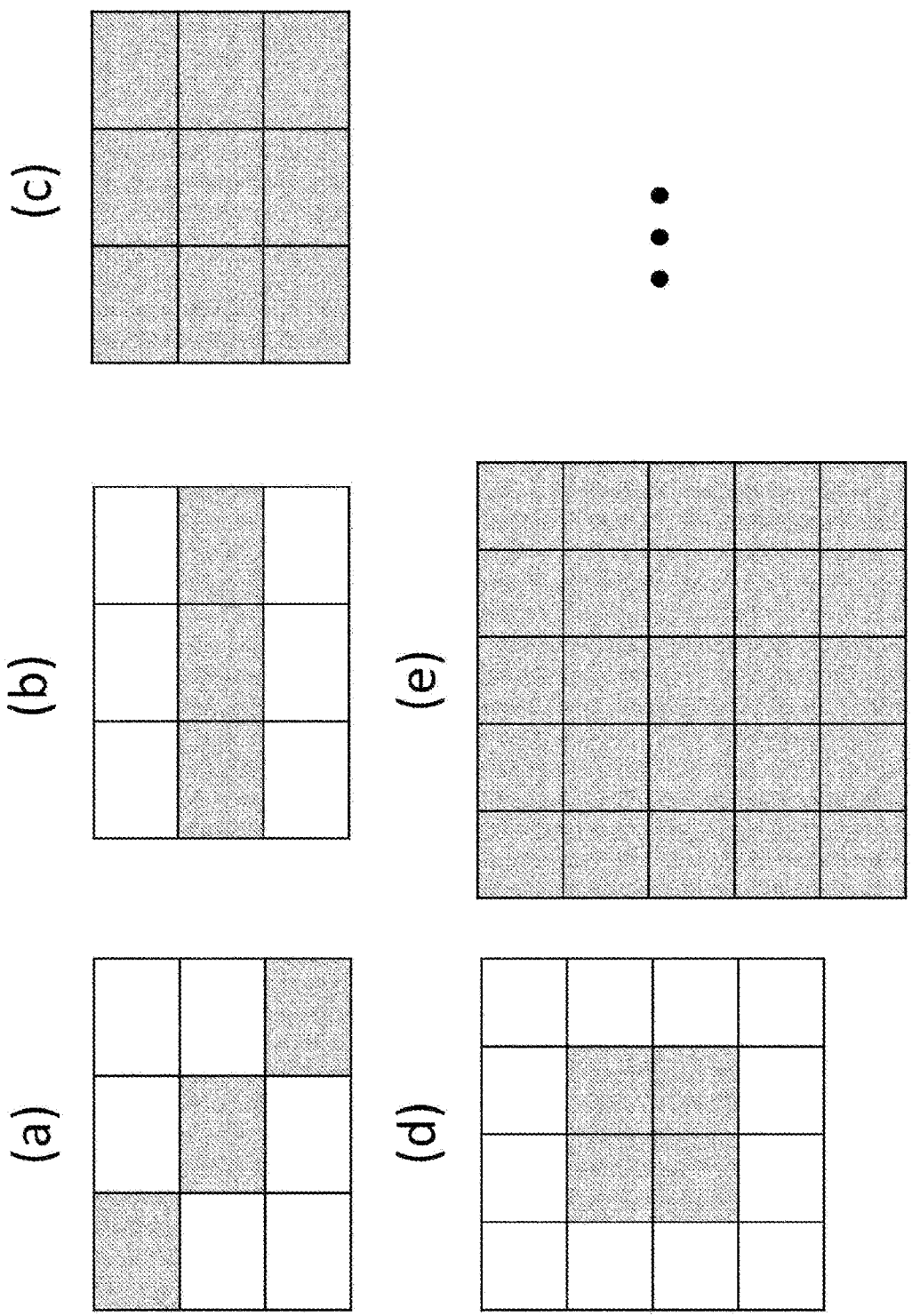
FIG. 3 is a diagram illustrating a modification of the method A.

Note that, here, the variable approximation of an image described above is not limited to a vertical direction. As shown in FIGS. 3(a) to (c), various directions such as a horizontal direction and an oblique direction are possible as well. Here, it is assumed that absorption ($a_0$), visibility (V), and phase ($\varphi$) are substantially the same in the three adjacent pixels as a specific example for the sake of description. As a matter of course, as shown in FIGS. 3(d) and (e), the absorption, the visibility, and the phase can be obtained by using the method according to the present invention, assuming that the absorption ($a_0$), the visibility (V), and the phase ($\varphi$) are substantially the same in a larger number of surrounding pixels. As a matter of course, the variable approximation can also be performed using different numbers of pixels, such as by assuming that the absorption and the visibility are substantially the same in five adjacent pixels and assuming that the phase is substantially the same in three adjacent pixels, for example.

In this manner, by solving a minimization problem by using data obtained through the variable approximation of the image, the phase can be obtained. Specifically, as shown below, the phase can be obtained by solving a problem of minimization of a difference between the data obtained according to Expression (5) shown above and a theoretical value according to Expression (1) shown above ($L^p$ (p≥0) norm minimization of a difference between a measured value and the theoretical value).

[Math. 6]

$$\min_{a_0, V, \phi} \sum_k |I_k - a_0(1 + V\cos(f(m, n + k) + \phi))|^p, \quad (6)$$
$$p \geq 0$$

Note that $I_k$ (k=0, ±1) represents a plurality of pieces of data obtained through the variable approximation of the same image as that of Expression (5). Here, if p=2, a least squares problem is to be solved.

Expression (6) for this problem can be solved by using various existing iterative methods (for example, the steepest descent method or the like), with an initial value of Expression (7) shown below being given.

[Math. 7]

$$\{a_0^{(0)}, V^{(0)}, \phi^{(0)}\} \quad (7)$$

Then, an obtained optimal solution $\{a_0, V, \varphi\}$ corresponds to the absorption ($a_0$), the visibility (V), and the phase ($\varphi$) to be obtained.

However, Expression (6) includes a trigonometric function of the variable $\varphi$, and is a minimization problem of a non-convex function. Thus, depending on the initial value, the convergence may result in a wrong solution (for example, a local minimum value). In light of this, in the present invention, when p≥1, a new analysis method as follows is proposed.

First, for ($a_0$, V, $\varphi$), variable conversion is performed as follows.

[Math. 8]

$$b_c \stackrel{\text{def}}{=} a_0 V \cos(\varphi), b_s \stackrel{\text{def}}{=} a_0 V \sin(\varphi) \qquad (8)$$

Through such conversion. Expression (6) for the problem can be expressed as follows.

[Math. 9]

$$\min_{a_0, b_c, b_s} \sum_k |I_k - (a_0 + b_c \cos(f(m, n+k)) - b_s \sin(f(m, n+k))|^p, \qquad (9)$$

$$p \geq 1$$

Expression (9) is a minimization problem of a convex function related to the three variables ($a_0$, $b_c$, $b_s$). Accordingly, as illustrated in FIG. 4, the convergence to a correct optimal solution is ensured without depending on the initial value to start with. After obtaining the optimal solutions $a_0$, $b_c$, and $b_s$, the absorption ($a_0$), the phase ($\varphi$), and the visibility (V) are obtained through the following variable conversion.

[Math. 10]

$$\phi = \tan^{-1}\left(\frac{b^s}{b^c}\right), V = \frac{\sqrt{b_c^2 + b_s^2}}{a_0} \qquad (10)$$

Thus, according to the phase imaging method of the present invention described above in detail (method A), the phase of the test object having a high spatial resolution can be acquired with at least a single imaging operation without a need of significant improvement in hardware through the use of an existing apparatus and equipment. In other words, in comparison to the conventional fringe-scanning method, the following can be achieved:

A. The requirement of high stability in the fringe-scanning method is eliminated owing to the motionlessness of the diffraction gratings.

B. The operation of the apparatus is simplified owing to the single imaging operation.

In addition, in comparison to the conventional Fourier transform method, the following can be achieved:

C. By maintaining a higher spatial resolution, an image can be provided that allows a larger number of fine internal structures to be seen (see FIG. 10(b) and FIG. 11(c) to be described later).

D. Further, in the analysis method, a solution is obtained through conversion to a minimization problem of a convex function, and thus regardless of a given specific initial value, an optimal solution is provided. This shall be significantly important in actual application, in particular.

Figure 5:
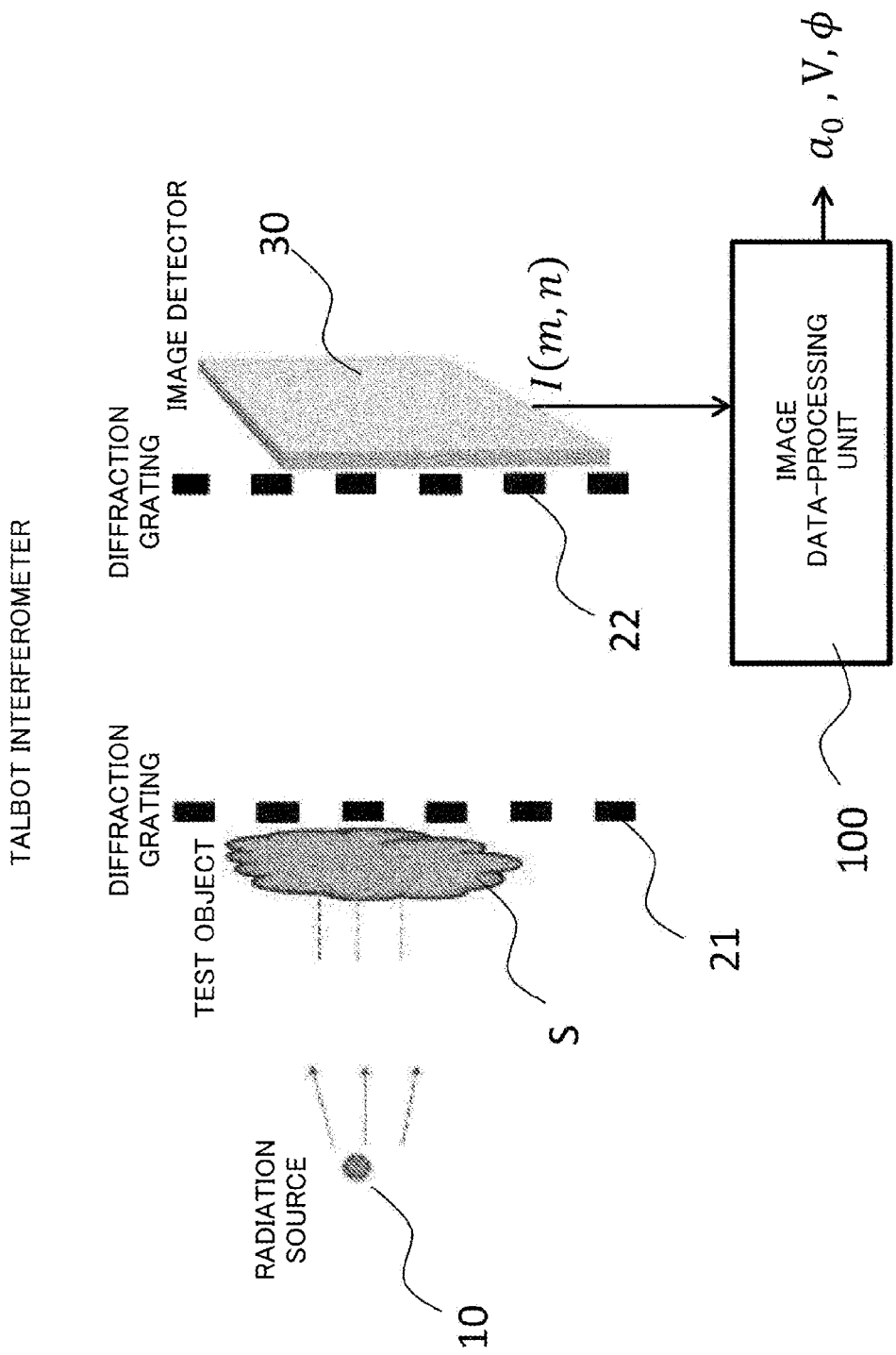
FIG. 5 is a diagram illustrating a configuration of a Talbot interferometer as an apparatus and equipment to which the method A can be applied.
Figure 6:
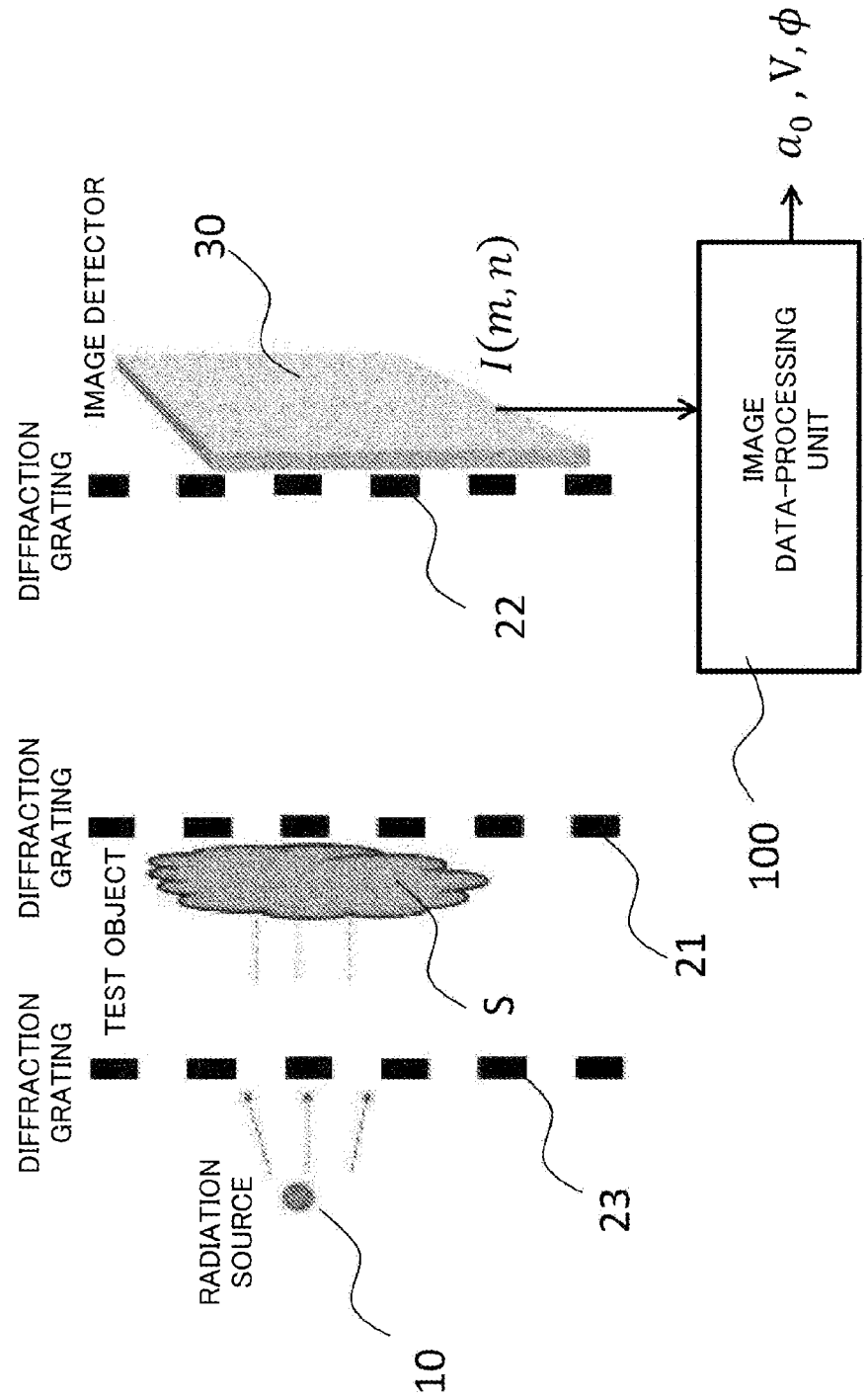
FIG. 6 is a diagram illustrating a configuration of a Talbot-Lau interferometer as an apparatus and equipment to which the method A can be applied.
Figure 7:
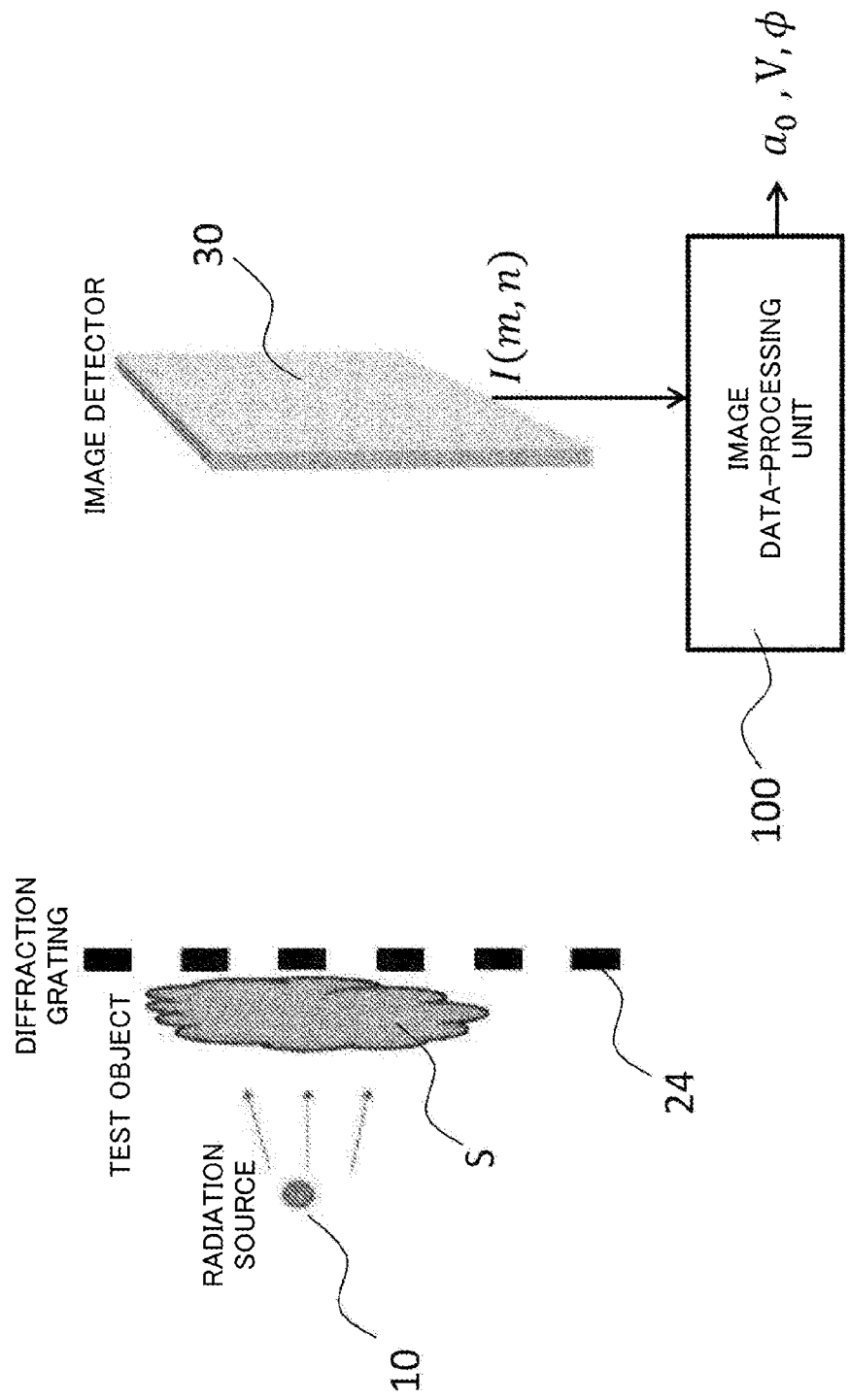
FIG. 7 is a diagram illustrating a configuration of a Lau interferometer as an apparatus and equipment to which the method A can be applied.

Equipment and Apparatus to which Method According to Present Invention can be Applied The phase imaging method described above (method A) can also be applied to an existing apparatus and equipment, and can be applied to, for example, as schematically illustrated in FIGS. 5 to 7 as well, a Talbot interferometer (FIG. 5), a Talbot-Lau interferometer (FIG. 6), a Lau interferometer (FIG. 7), or the like that forms interference fringes by using an X-ray source (or a neutron radiation source).

As illustrated in FIG. 5, an X-ray Talbot interferometer uses an X-ray source 10 that generates X-rays, and includes a phase diffraction grating 21 that causes interference of the X-rays to be generated, an absorption diffraction grating 22 that converts interference intensity distribution caused in a test object S into moiré intensity distribution, and an X-ray detector 30. Note that, in the apparatus, a periodic image (self image) similar to the phase grating is generated due to the interference at a position that is apart from the grating by a certain distance. This phenomenon is referred to as the Talbot effect. Further, the second diffraction grating is disposed at the position where the self image is generated, to thereby form moiré interference fringes. Thus, what is directly measured in the Talbot interferometer is not phase but is intensity distribution of the moiré interference fringes deformed due to the test object, and intensity distribution I (m, n) measured with an image detector is, for example, transmitted to an image data-processing unit including a CPU as an arithmetic element, a RAM and a ROM as storage means, and the like, and the results are output as the absorption ($a_0$), the visibility (V), and the phase ($\varphi$) through predetermined arithmetic processing. Note that the two-dimensional image detector 30 that detects the interference fringes in these interferometers is configured in such a manner that a large number of pixels as semiconductor X-ray detection elements are disposed flat, and for example, an electromagnetic wave detector and an image detector disclosed in JP 2002-26300 A or the like may be adopted. Further, from each pixel, X-ray intensity (I) described above is output.

Further, the Talbot-Lau interferometer illustrated in FIG. 6 further includes a diffraction grating 23 in front of the X-ray source 10. Further, the Lau interferometer illustrated in FIG. 7 includes a phase grating 24 between the X-ray source and the test object. With these interferometers as well, in a manner similar to the above, the intensity distribution I (m, n) measured in the image detector 30 is, for example, transmitted to the image data-processing unit 100 including a CPU as an arithmetic element, a RAM and a ROM as storage means, and the like, and the results are output as the absorption ($a_0$), the visibility (V), and the phase ($\varphi$) through predetermined arithmetic processing.

In this manner, the phase imaging method according to the present invention can also be easily applied to an existing apparatus and equipment, and through a predetermined arithmetic operation using imaged data (intensity signal (I)) obtained using the apparatus and equipment by the image data-processing unit, the phase of the test object having a high spatial resolution can be acquired from at least a single imaging operation.

Example 2

Method B

Subsequently, the present invention provides a method with which a solution having higher accuracy than that of the method A described above can be obtained with at least a single imaging operation when imperfect phase information is known in advance. Here, the known phase information described above can be acquired based on a phase image that is obtained by using the Fourier transform method as a conventional method, the method A according to the present invention described above, and the like.

In the following description of the method B according to the present invention, the known phase information is referred to as an "approximation phase image".

With this method as well, in a manner similar to the method A according to the invention, phase is obtained by solving a minimization problem. Here, the method B differs from the method A according to the invention described above in that a minimization problem of a weighted energy function is solved by using a weight function W (m, n). Here, the method will be described with one arbitrarily selected pixel (m, n) being fixed. Calculation can be performed in a similar manner at other positions as well. As for the weight, an approximation phase image is used, and points having close phase values (or structures) are searched for in a wide range in the pixel (m, n), and the more similar the points are, the greater weight is given. Further, the following weighted minimization problem is solved.

[Math. 11]

$$\min_{a_0, b_c, b_s} \sum_{l,k} W_{l,k} |I_{l,k} - (a_0 + b_c \cos(f(m+l, n+k)) - b_s \sin(f(m+l, n+k))|^p, \; p \geq 0 \quad (11)$$

Note that $I_{l,k}$ (l, k=0, ±1, . . . ) represents a plurality of pieces of data obtained according to an approximation (as in Expression (5) shown above), and $b_c$ and $b_s$ are variables defined in Expression (8). The weight $W_{l,k}$ is defined as follows.

[Math. 12]

$$\ldots, W_{0,-1} = W(m, n-1), W_{0,0} = W(m, n), \ldots, W_{1,0} = W(m+1, n), \ldots \quad (12)$$

Here, W (m+l, n+k) (l, k=0, ±1, . . . ) represents similarity between phase values of a target pixel (m, n) whose phase is to be obtained and a pixel (m+l, n+k) (l, k=0, ±1, . . . ), and a calculation method thereof will be described later.

Figure 8:
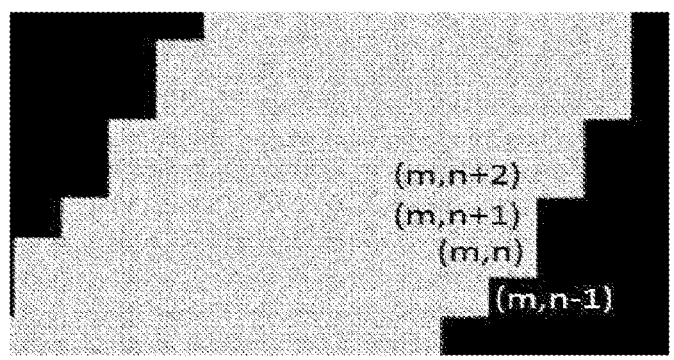
FIG. 8 is a diagram illustrating weights of a method B according to another embodiment (Example 2) of the present invention.

Here, the effect of the weight will be described. For example, it is assumed that the pixel (m, n) is a boundary between an object and another object as shown in FIG. 8, and the phase value of the pixel (m, n) is significantly different from that of an adjacent pixel (m, n−1). In this case, the assumption of Expression (3) shown above is incorrect. Thus, an error of a phase image obtained by using the data of the pixel (m, n−1) is also increased.

Figure 9:
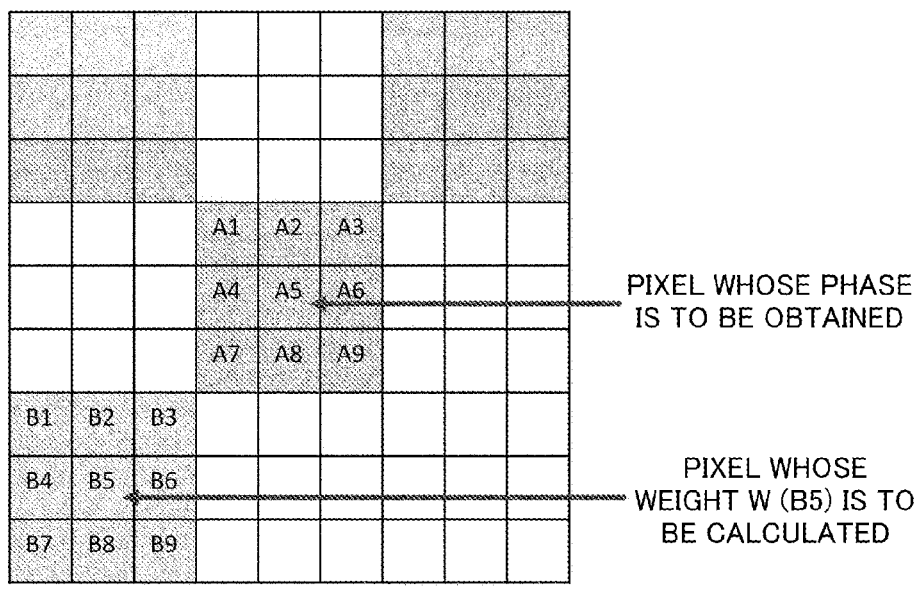
FIG. 9 is a diagram illustrating calculation of the weights of the method B.

In the method B according to the present invention, this problem is alleviated by using the weight $W_{l,k}$. Specifically, first, as illustrated in FIG. 9, the weight is calculated by using the approximation phase image. The phase value of the pixel (m, n) is significantly different from that of the pixel (m, n−1), and the pixel (m, n) and the pixel (m, n−1) are not similar to each other, thus causing the weight to be smaller. Thus, in Expression (12) shown above, the weight $W_{0,-1}$ is as follows.

[Math. 13]

$$W_{0,-1}(m, n-1) \approx 0 \quad (13)$$

In this case, by using the weight in Expression (11) shown above, the data of the pixel (m, n−1) is eliminated from the calculation. This signifies that the approximation of Expression (3) shown above is converted to a more correct approximation. As a result, more accurate phase can be obtained even if there is a discontinuous boundary.

Subsequently, the calculation method of the weight function W (m, n) described above will be described. As for the calculation method of the weight, various weights can be used. As one example thereof, in the following, a specific weight calculation method using non-local means will be described.

For example, it is assumed that there is an approximation phase image as shown in FIG. 9. A situation of obtaining a phase value in a target pixel (A5) is considered. In this case, the weight of each of the surrounding pixels is determined by the phase value (or the structure) of the approximation phase image. For example, as illustrated in FIG. 9 as well, the weight of each pixel (B5) is determined by using a target block around the target pixel (A5) and a reference block around (B5) as follows.

[Math. 14]

$$W(B5) = \frac{1}{C} \exp\left(-\sum_m (\phi(Am) - \phi(Bm))^2 / h_1^2\right) \quad (14)$$

Note that C represents a normalization constant for causing the sum of the weights of all of the operating pixels to be one.

Here, $h_1 \geq 0$ is a parameter that is defined in advance. Expression (14) is a weight according to similarity between blocks, and the more similar the phase values (or the structures) are, the greater weight is given.

Experiment Results

Next, to verify the effect of the phase imaging method and the phase imaging apparatus according to the present invention described above, processing with the methods A and B was performed according to the present invention by using a numerical phantom and an X-ray differential phase image. How to create a contrast image will be described below. In the experiment, first, a single piece of interference fringe data is generated according to Expression (1) by using phase ($\varphi$), absorption ($a_0$), and visibility (V) of a hypothetical object. Phase images obtained from a resultant interference fringe image by using the Fourier transform method and the present invention (the method A or the method B) are shown.

Figure 10:
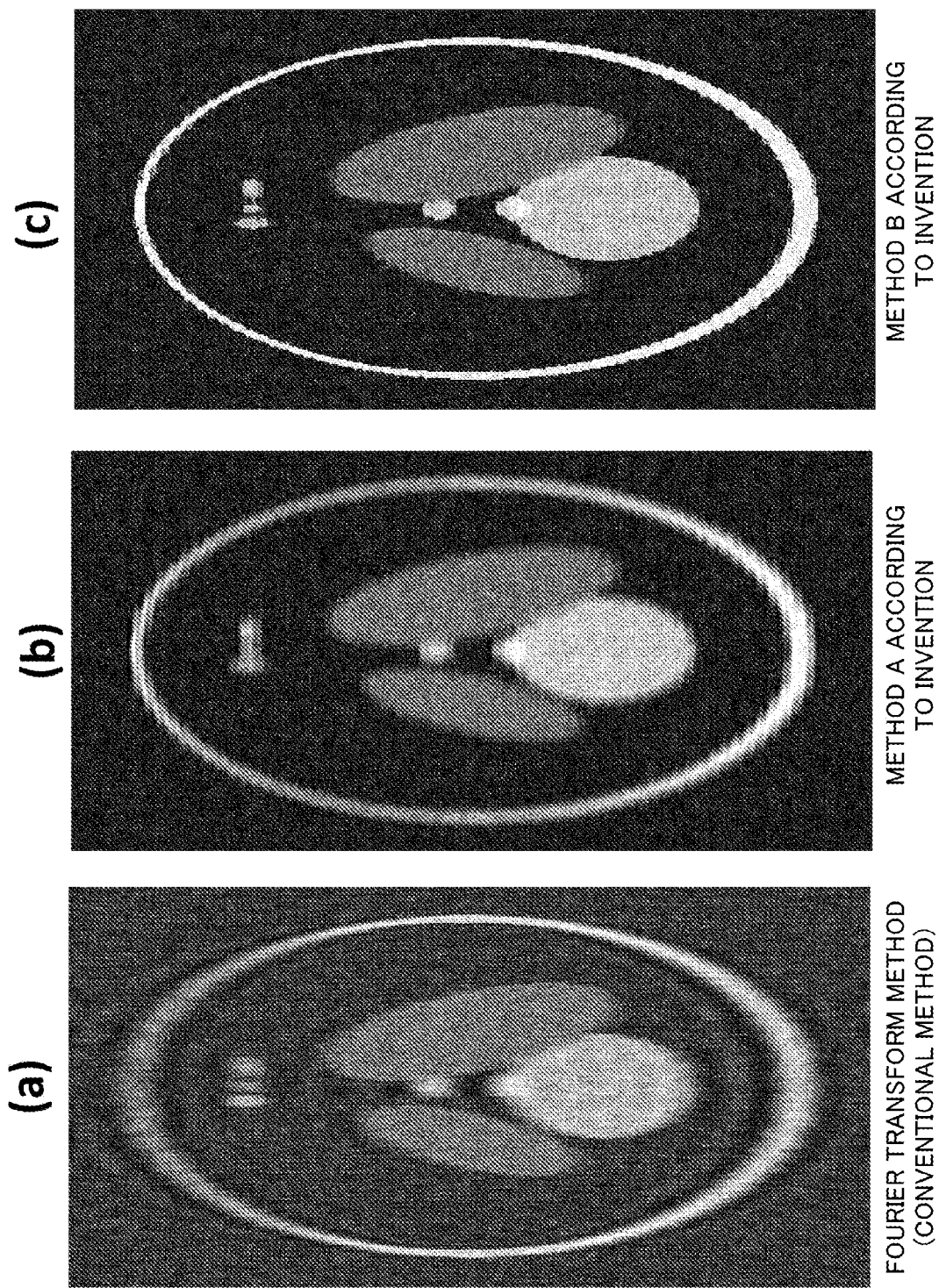
FIG. 10 is a diagram illustrating an example in which recovery of phase is performed by using a numerical phantom by using the methods A and B according to the present invention, in comparison to a conventional technology.

FIG. 10 illustrates an example in which phase recovery was performed by using a numerical phantom that simulates a CT image inside a human body; FIG. 10(a) is a phase image obtained by using the Fourier transform method as a conventional method, FIG. 10(b) is a phase image obtained by using the method A according to the present invention, and FIG. 10(c) is a phase image obtained by using the method B according to the present invention. As is apparent from these phase images, the phase image obtained by using the method A or the method B according to the present invention clearly has a higher spatial resolution than the phase image obtained by using the conventional Fourier transform method, and in addition, it can be understood that the phase image obtained by using the method B has more accurate boundaries and details than the phase image obtained by using the method A.

Figure 11:
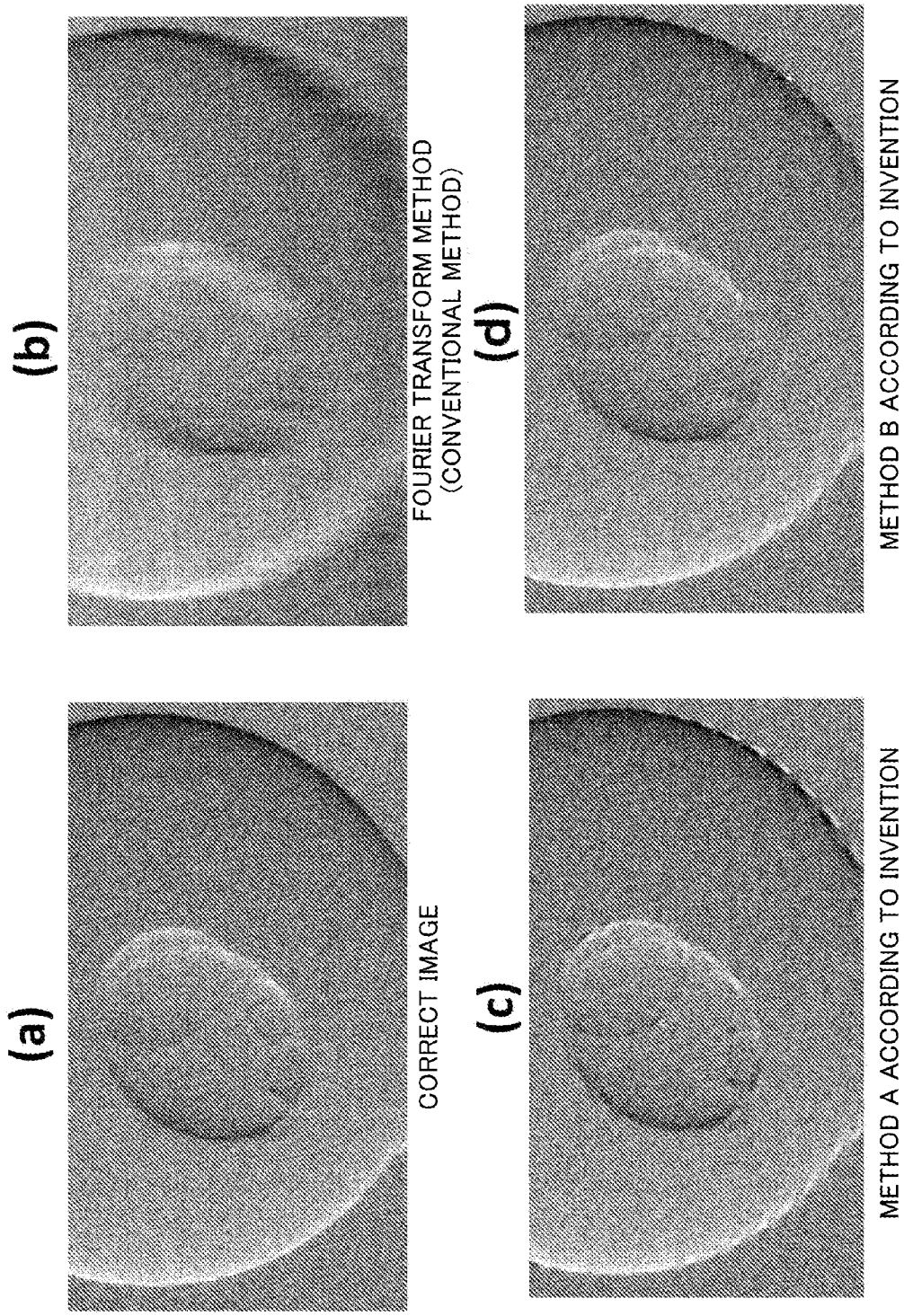
FIG. 11 is a diagram illustrating a phase image of polymer spheres obtained by using the methods A and B according to the present invention, in comparison to a conventional technology.

FIG. 11 illustrates results of simulation which was performed by using a differential phase image of polymer spheres (diameter of 5/16 inches), and illustrates, as well as (a) a phase image (correct phase image) of a test object, (b) a phase image obtained by using the Fourier transform method, (c) a phase image obtained by using the method A according to the present invention, and (d) a phase image obtained by using the method B according to the present invention. As is apparent from the results as well, with the conventional method (Fourier transform method) of FIG. 11(b), the resolution is significantly lowered. On the other hand, with the method A according to the present invention of FIG. 11(c), the resolution is higher as a whole, and further, even the boundaries are substantially correctly recovered with the method B according to the present invention of FIG. 11(d).

FIG. 12 illustrates results of phase recovery which was performed by using real data of polymers imaged by a Talbot interferometer. The imaging was performed in Spring-8 (large-scale synchrotron radiation facility). The size of the captured image is 2048×1024 pixels, and a period of the moiré fringes is 22 pixels. FIG. 12(a) is a phase image obtained by using the Fourier transform method as a conventional method, FIG. 12(b) is a phase image obtained by using the method A according to the present invention, and FIG. 12(c) is a phase image obtained by using the method B according to the present invention. As is apparent from these phase images, the phase image obtained by using the method A or the method B according to the present invention is less affected by noise and clearly has a higher spatial resolution than the phase image obtained by using the conventional Fourier transform method, and in addition, it can be understood that the phase image obtained by using the method B has more accurate boundaries and details than the phase image obtained by using the method A.

As has been described in detail in the above, with the phase imaging method according to the present invention, the phase of the test object can be acquired with high accuracy with at least a single imaging operation.

In comparison to the conventional fringe-scanning method,

A. The requirement of high stability in the fringe-scanning method is eliminated because the movement of the diffraction gratings is not required.

B: The operation of the apparatus and the equipment is further simplified because the phase image can be obtained with a single imaging operation.

C: Dynamic measurement for a moving object or a changing object can be more correctly performed because the phase image can be obtained with a single imaging operation.

In addition, in comparison to the conventional Fourier transform method,

D: By maintaining a higher spatial resolution, an image can be provided that allows a larger number of fine internal structures to be seen.

E: Although the accuracy of the method according to the present invention depends on the period of imaged interference fringes, a phase image can be obtained such that the accuracy is not significantly lowered even when the period is greater than the period usually used in the Fourier transform method (by approximately five or six pixels per period) (for example, several tens of pixels per period). In the X-ray phase imaging using the diffraction gratings, when the period of the moiré fringes is increased, the visibility is significantly improved. Thus, in the present method, an image with more satisfactory image quality than that of the conventional method can be obtained.

With the method B according to the present invention, specific weight calculation is performed by using the non-local means. As a matter of course, however, various methods can be applied. Examples of the methods include a filter such as a bilateral filter and a method other than the filter in which a greater weight is obtained as the images are more similar to each other.

With the method B according to the present invention described above, the weight is calculated by using the approximation phase image. The approximation phase image is not limited to the image according to the present method A or the Fourier transform method. As a matter of course, the phase image obtained by using any other method can also be used for the weight calculation. Examples of the images include an image of the same object imaged by using another apparatus or hardware, previous measurement data (if any) or the like, an image of another known object with a similar structure, and the like. In addition, even if the approximation phase image is not available, it is possible to use the position information of a discontinuous place of the object. For example, an absorption captured image of the same object is used.

Other Equipment and Apparatus to which Present Invention can be Applied

As described above, the phase imaging method and the phase imaging apparatus according to the present invention shall be preferably used in a high-speed phase CT imaging apparatus or the like using a Talbot interferometer as illustrated in FIG. 12 as well, particularly by exploiting convenience of its operation (motionlessness of diffraction gratings). Note that, here, fringe scan is not performed.

Note that the technology to which the present invention can be applied is not limited to those described above, and application is also possible to, for example, a phase X-ray CT that performs image generation of phase shift distribution based on line integral data of phase shift distribution in a case of X-ray irradiation, a PET (positron emission CT) or a SPECT (single photon radiation CT) as a nuclear medical imaging apparatus for generating an image of radioactive drug distribution administered into a body, a CT using wave motions of ultrasonic waves, microwaves, acoustic waves, earthquake waves, or the like, an electron beam CT, magnetic resonance imaging (MRI) using image reconfiguration from projected data, and the like. In other words, the term "object" or "image" in the present invention refers to spatial distribution of a physical amount to be imaged.

Further, numerical values of a phase shift, a phase shift of a quantum beam, diffraction, or an image including diffraction are extracted from a plurality of sets acquired through addition of an optical element or a position change thereof, and the phase value can also be recovered by using the extracted numerical values of the phase shift of the quantum beam, the diffraction, or the image including the diffraction.

INDUSTRIAL APPLICABILITY

The present invention provides a phase imaging method of obtaining an image of a test object by using a phase change that is obtained through radiation of quantum beams such as X-rays, and a phase imaging apparatus that uses the phase imaging method.

REFERENCE SIGNS LIST

10 . . . Radiation source
21-24 . . . Diffraction (phase) grating
S . . . Test object
100 . . . Image data-processing unit

The invention claimed is:
1. A phase imaging method, comprising:
causing a quantum beam from a radiation source to be incident on a detector through a test object and at least one phase grating, and obtaining a phase image of the test object, based on intensity distribution of a beam in a pixel constituting the detector, wherein the intensity distribution of the beam at least includes information of absorption ($a_0$), visibility (V), and phase ($\varphi$), at least three adjacent pixels are assumed to have a substantially identical value for each of the absorption ($a_0$), the visibility (V), and the phase ($\varphi$) through variable approximation of an image, and the absorption, the visibility, and the phase are obtained, based on at least one measurement image.

2. The phase imaging method according to claim 1, wherein the intensity distribution of the beam in the pixel (m, n) of the detector is expressed as follows, $$I(m,n)=a_0(m,n)(1+V(m,n)\cos(f(m,n)+\varphi(m,n)))$$

where $a_0$ represents absorption, V represents visibility, $\varphi$ represents phase, and f represents an interference fringe on a background, and the absorption, the visibility, and the phase are obtained based on at least one measurement image by setting as follows, $$\ldots = a_0' = a_0 = a_0'' = \ldots$$

$$\ldots = V' = V = V'' = \ldots$$

$$\ldots = \varphi' = \varphi = \varphi'' = \ldots$$

where, in the variable approximation of the image, . . . , $a_0'$, $a_0$, $a_0''$ . . . represents the absorption, . . . , V', V, V'' . . . represents the visibility, and . . . , $\varphi'$, $\varphi$, $\varphi''$ . . . represents the phase.

3. The phase imaging method according to claim 1, wherein the absorption, the visibility, and the phase are obtained by using $L^p$ ($p \geq 0$) norm minimization of a difference between a measured value and a theoretical value.

4. The phase imaging method according to claim 3, wherein in the $L^p$ norm minimization, for $p \geq 1$, a non-convex minimization problem is converted into a convex function minimization problem through variable conversion to obtain the absorption, the visibility, and the phase.

5. A phase imaging method, comprising:

causing a quantum beam from a radiation source to be incident on a detector through a test object and at least one phase grating, and obtaining a phase image of the test object, based on intensity distribution of a beam in a pixel constituting the detector, wherein weighting processing is performed that gives a weight depending on similarity between each pixel and a phase value (or structure) of the pixel to be obtained by using an approximation phase image given in advance, and subsequently, absorption, visibility, and phase are obtained based on at least one measurement image by using the weight.

6. The phase imaging method according to claim 5, wherein the absorption, the visibility, and the phase are obtained based on the at least one measurement image by setting as follows, $$\ldots = a_0' = a_0 = a_0'' = \ldots$$

$$\ldots = V' = V = V'' = \ldots$$

$$\ldots = \varphi' = \varphi = \varphi'' = \ldots$$

where, in a range in which the phase values (or the structures) are similar to each other, . . . , $a_0'$, $a_0$, $a_0''$ . . . represents the absorption, . . . , V', V, V'' . . . represents the visibility, and . . . , $\varphi'$, $\varphi$, $\varphi''$ . . . represents the phase.

7. The phase imaging method according to claim 6, wherein the absorption, the visibility, and the phase are obtained by using weighted $L^p$ ($p \geq 0$) norm minimization of a difference between a measured value and a theoretical calculation value.

8. The phase imaging method according to claim 7, wherein in the weighted $L^p$ norm minimization, for $p \geq 1$, a non-convex minimization problem is converted into a convex function minimization problem through variable conversion to obtain the absorption, the visibility, and the phase.

9. The phase imaging method: wherein the approximation phase image given in advance is a phase image obtained by using the method according to claim 5.

10. The phase imaging method according to claim 5, wherein the approximation phase image given in advance is a phase image obtained by using a Fourier transform method.

11. The phase imaging method according to claim 5, wherein the approximation phase image given in advance is an image of an identical object captured in another apparatus, previous measurement data, or an image of another known object with a similar structure.

12. The phase imaging method according to claim 5, wherein the weighting is performed by using calculation using non-local means, by using a filter such as a bilateral filter, or by using a method in which a greater weight is obtained as images are more similar to each other.

13. The phase imaging method according to claim 5, wherein instead of the approximation phase image, an absorption captured image of a discontinuous place of the test object is used.

14. A phase imaging apparatus, comprising:

a radiation source configured to generate a quantum beam;

a holder configured to hold a test object to which a beam from the radiation source is radiated;

a detector configured to receive the beam from the test object through at least one phase grating; and a processing unit configured to obtain a phase image of the test object, based on intensity distribution of the beam in a pixel constituting the detector, wherein the processing unit obtains absorption, visibility, and phase by executing the phase imaging method according to claim 1.

15. A phase imaging apparatus, comprising:

a radiation source configured to generate a quantum beam;

a holder configured to hold a test object to which a beam from the radiation source is radiated;

a detector configured to receive the beam from the test object through at least one phase grating; and a processing unit configured to obtain a phase image of the test object, based on intensity distribution of the beam in a pixel constituting the detector, wherein the processing unit obtains absorption, visibility, and phase by executing the phase imaging method according to claim 5.

\* \* \* \* \*